United States Patent
Kim

(10) Patent No.: US 6,582,356 B2
(45) Date of Patent: Jun. 24, 2003

(54) METHOD FOR MAGNIFYING PENIS AND METHOD FOR USING ENDOSCOPE FOR THE SAME

(76) Inventor: Jae Young Kim, #A-2 Chunga Sports Center, 575 Shinsa-dong, Gangnam-ku, Seoul, 135-120 (KR)

( * ) Notice: Subject to any disclaimer, the term of this patent is extended or adjusted under 35 U.S.C. 154(b) by 25 days.

(21) Appl. No.: 09/951,453

(22) Filed: Sep. 14, 2001

(65) Prior Publication Data

US 2002/0133056 A1 Sep. 19, 2002

(30) Foreign Application Priority Data

Mar. 14, 2001 (KR) .......................................... 2001-13142

(51) Int. Cl.$^7$ ................................................ A61B 19/00
(52) U.S. Cl. ........................................ 600/40; 128/898
(58) Field of Search ..................... 128/898; 600/38–41; 623/7, 11, 12, 66

(56) References Cited

U.S. PATENT DOCUMENTS 5,921,246 A * 7/1999 Cho ............................ 128/898
6,173,714 B1 * 1/2001 Cho ............................ 128/898

* cited by examiner

Primary Examiner—Samuel G. Gilbert
(74) Attorney, Agent, or Firm—Greenblum & Bernstein, P.L.C.

(57) ABSTRACT

A method for magnifying penis and a method for using endoscope for the same are disclosed. The method for magnifying penis using an endoscope includes the steps of: removing a patient's pubic hair portion and cutting skin to a dermis fat layer in length of 1–2 cm; magnifying a portion between epidermis and the dermis fat layer to the penis through the cut portion using a surgical operation tool to secure a space; inserting the endoscope through the secured space and checking whether or not nerves and blood vessel exist vertically; inserting a magnifying material through the secured space if the nerves and blood vessel do not exist vertically; fastening the magnifying material in a proper position while picking up the skin of the penis and the magnifying material at the same time if the magnifying material is inserted; and stitching the cut portion when the magnifying material is fastened. The method does not show any indication of surgical operation on the penis and have no harmful side effects by inserting dermis fat obtained from the patient's hips through a pubic hair portion after cutting the pubic hair portion, and moreover, can prevent the patient's nerves and blood vessel during the penile augmentation procedure, since a doctor magnifies the penis while checking the condition of the nerves and the blood vessel through the endoscope.

4 Claims, 5 Drawing Sheets

[Drawing]
[FIG. 1]
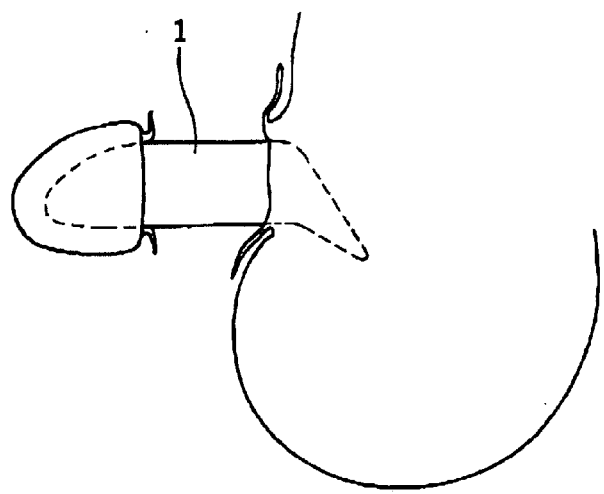
[FIG. 2]
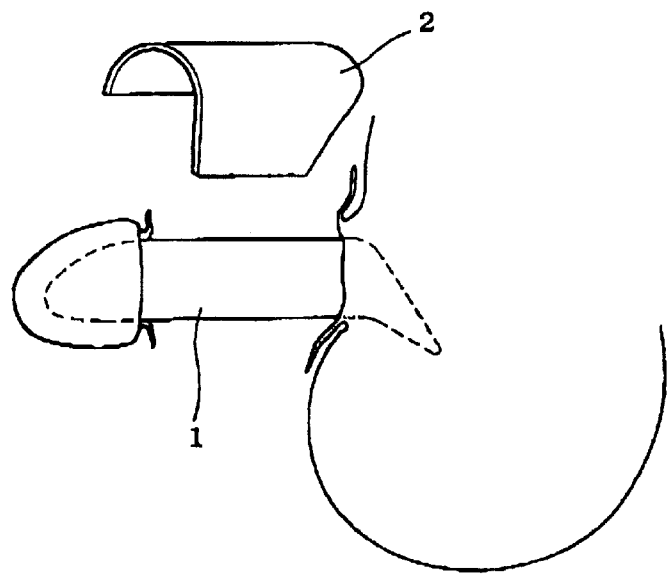

[FIG. 3]
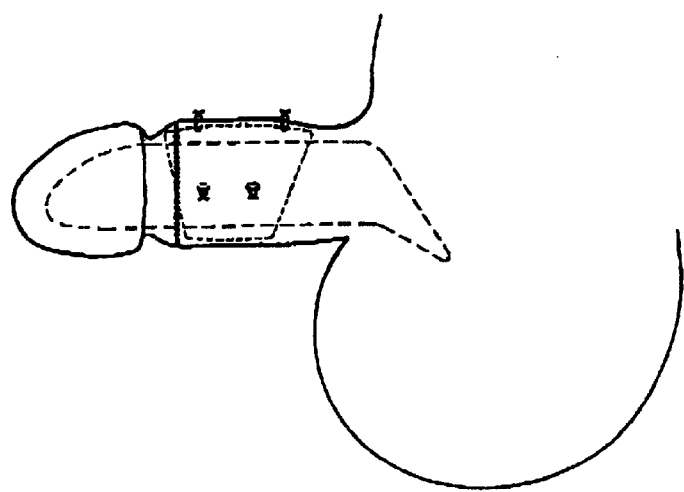
[FIG. 4]
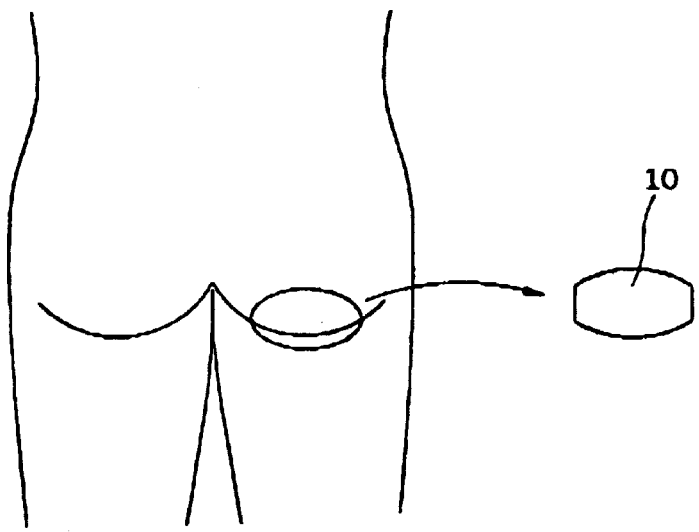

[FIG. 5]
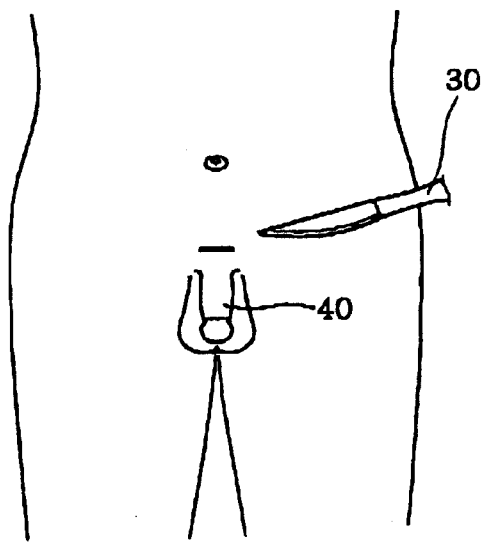
[FIG. 6]
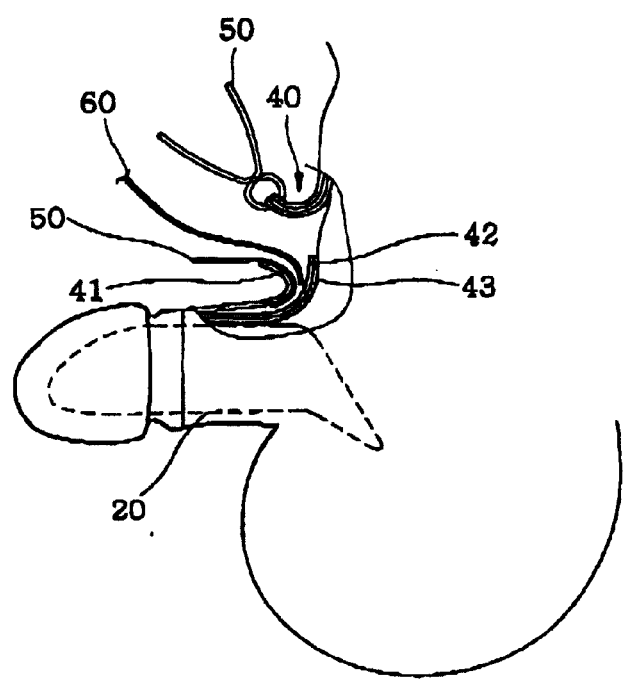

[FIG. 7]
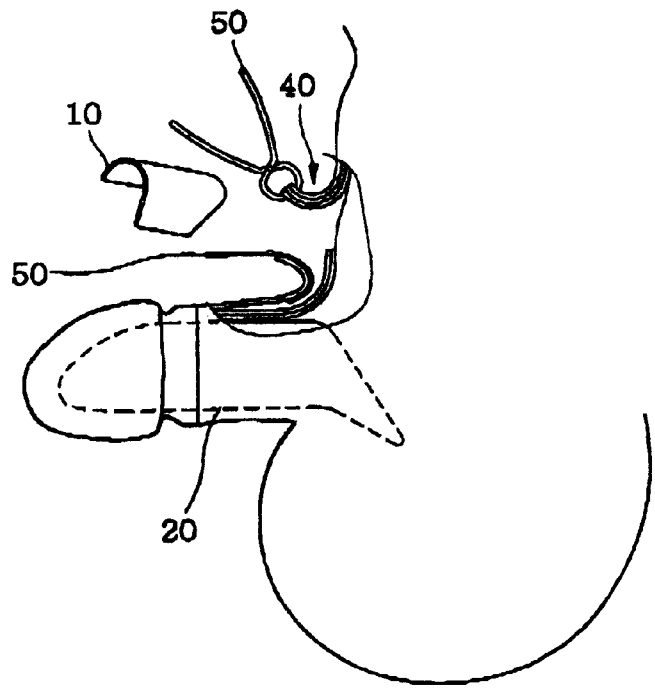
[FIG. 8]
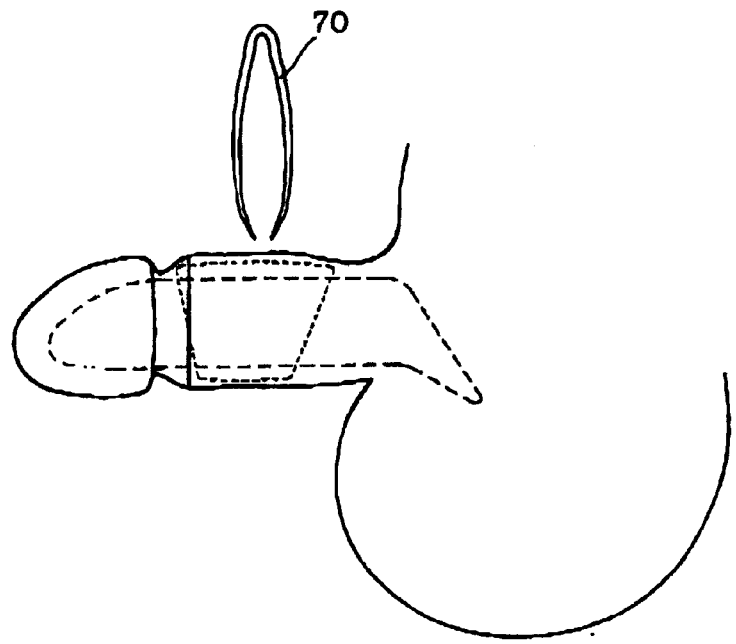

[FIG. 9]
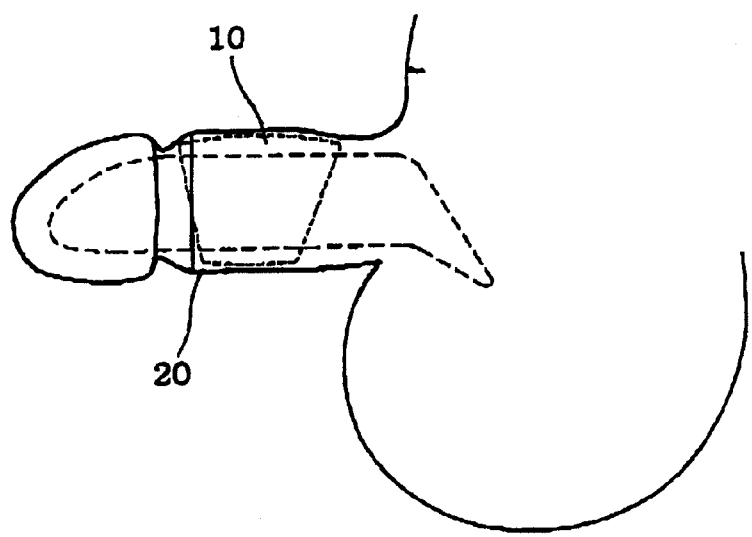

METHOD FOR MAGNIFYING PENIS AND METHOD FOR USING ENDOSCOPE FOR THE SAME

BACKGROUND OF THE INVENTION

1. Field of the Invention

The present invention relates to a method for magnifying a penis and a method for using an endoscope for the same, and more particularly, to a method for magnifying a penis and a method for using an endoscope for the same, which do not show any indication of a surgical operation on the penis and cause no harmful side effects by way of inserting a magnifying material through a pubic hair portion without directly operating on the penis, and which can prevent a patient's nerves and blood vessel from being injured during a penis magnifying process, since a doctor magnifies the penis while checking the condition of the nerves and the blood vessel through the endoscope.

2. Background of the Related Art

In general, for the penile augmentation, there are a method of inserting solid silicone after a local anesthesia and a method of grafting a dermis fat. The penis is the man's body part where the most body contact is made and friction is severely produced during sexual acts. Therefore, compared with the silicone inserting operation method, the self-dermis fat grafting operation method and the penile augmentation method using special materials for artificial blood vessel are much safer and of practical use permanently.

The penile augmentation, generally used these days, means a surgical operation of grafting a patient's own dermis fat. The method for grafting the dermis fat includes the steps of ripping off the dermis fat from the patient's hips, incising an upper portion of the penis 1 as shown in FIGS. 1 through 3, and stitching up the incised portion after grafting the ripped dermis fat 2. However, such conventional operation methods have a problem that the stitched portion is burst open when the penis erects, since the seam of a wound (surgically operated mark) remains permanently after the penis operation.

Furthermore, the conventional operation methods have other problems that the stitched portion is inflamed in case of the patients of about 5%, the grafted dermis fat tissue may become necrotic, there occurs an arterial calcification that a portion of the penis is hardened, and especially, there is every probability that harmful side effects are caused in the stitched portion of the penis.

SUMMARY OF THE INVENTION

Accordingly, the present invention is directed to a method for magnifying penis and a method for using endoscope for the same that can substantially obviate one or more problems due to limitations and disadvantages of the related art.

An object of the present invention is to provide a method for magnifying penis and a method for using endoscope for the same, which do not show any indication of surgical operation on the penis and cause no harmful side effects not by directly applying a dermis fat obtained from a patient's hips to the patient's penis but by way of inserting magnifying material through a pubic hair portion after cutting the pubic hair portion Another object of the present invention is to provide a method for magnifying penis and a method for using endoscope for the same, which can prevent the patient's nerves and blood vessel during a penis magnifying process because a doctor magnifies the penis while checking the condition of the nerves and the blood vessel through the endoscope.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, a method for magnifying penis using endoscope includes the steps of: removing a patient's pubic hair portion and cutting skin to a dermis fat layer in length of 1–2 cm; magnifying a portion between epidermis and the dermis fat layer to the penis through the cut portion using a surgical operation tool to secure a space; inserting an endoscope through the secured space and checking whether or not the nerves and blood vessel exist vertically; inserting magnifying material through the secured space if the nerves and blood vessel do not exist vertically; fastening the magnifying material in a proper position while picking up the skin of the penis and the magnifying material at the same time if the magnifying material is inserted; and stitching the cut portion when the magnifying material is fastened The magnifying material is the dermis fat obtained from the patient's hips in a plate shape.

Here, in the step of checking whether or not the nerves and blood vessel exist vertically, if the nerves and blood vessel do not exist vertically, the method for magnifying penis further includes the steps of magnifying a portion between a subcutaneous fat layer of the cut portion and the dermis fat layer or the inside of the subcutaneous fat layer, checking through the endoscope whether or not the nerves and blood vessel exist vertically, and inserting the magnifying material through the magnified portion if the nerves and blood vessel do not exist vertically.

A method using an endoscope for magnifying penis includes the steps of: magnifying a portion between epidermis and the dermis fat layer after cutting the skin and checking through the endoscope whether or not the nerves and blood vessel exist vertically; and magnifying a portion between a subcutaneous fat layer and the dermis fat layer or the inside of the subcutaneous fat layer, checking through the endoscope whether or not the nerves and blood vessel exist vertically, and inserting the magnifying material if the nerves and blood vessel do not exist vertically.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings;

FIG. 1 illustrates a view showing a state that an upper portion of a patient's penis is ripped off in a conventional penile augmentation method;

FIG. 2 illustrates a view showing a state that a dermis fat is covered on the ripped penis of FIG. 2;

FIG. 3 illustrates a view showing a state that the dermis fat is stitched after covered in the conventional penile augmentation method;

FIG. 4 illustrates a view showing a state that the dermis fat of the patient's hips is obtained in a penile augmentation method according to the present invention;

FIG. 5 illustrates a view showing a state that the patient's skin is cut with a knife after removing a pubic hair portion of the penis in the penile augmentation method according to the present invention;

FIG. 6 illustrates a view showing a state that a doctor checks the nerves and blood vessel through an endoscope while performing the penile augmentation according to the present invention;

FIG. 7 illustrates a view showing a state that the dermis fat is inserted in the penile augmentation method according to the present invention;

FIG. 8 illustrates a view showing a state that the dermis fat is fastened in the penile augmentation method according to the present invention; and FIG. 9 illustrates a view showing a state that the dermis fat is stitched after fastened in the penile augmentation method according to the present invention.

DETAILED DESCRIPTION OF THE PREFERRED EMBODIMENT

Reference will now be made in detail to the preferred embodiments of the present invention, examples of which are illustrated in the accompanying drawings.

Referring to FIGS. 4 through 9, a method for magnifying penis and a method for using endoscope for the same will be described in detail.

FIG. 4 illustrates a view showing a state that a dermis fat of the patient's hips is obtained in the penile augmentation method according to the present invention. FIG. 5 illustrates a view showing a state that the patient's skin is cut with a knife after removing a pubic hair portion of the penis. FIG. 6 illustrates a view showing a state that a doctor checks the nerves and blood vessel through an endoscope while performing the penile augmentation according to the present invention. FIG. 7 illustrates a view showing a state that the dermis fat is inserted in the penile augmentation according to the present invention. FIG. 8 illustrates a view showing a state that the dermis fat is fastened in the penile augmentation according to the present invention. FIG. 9 illustrates a view showing a state that the dermis fat is stitched after fastened in the penile augmentation method according to the present invention.

First, as shown in FIG. 3, a dermis fat 10 is obtained from the patient's hips in a plate shape and stored in physiological salt solution or in a low temperature. At this time, a size and a thickness of the dermis fat 10 are in proportion to a size of the patient's penis.

After that, as shown in FIG. 5, the pubic hair portion located on the penis 20 under the navel is removed, and then, skin 40 is cut to a lower part of a subcutaneous fat layer 43 in length of about 1–2 cm using a knife 30.

When the skin 40 is ripped off, as shown in FIG. 6, a portion between an epidermis 41 and a dermis fat layer 42 is magnified to the penis 20 to secure a space while the cut portion is magnified using a surgical operation tool 50. An endoscope 60 is inserted through the secured space, and then, the doctor checks whether or not the nerves and blood vessel exist vertically. If the nerves and blood vessel do not exist vertically, the dermis fat 10 is inserted through the secured space as shown in FIG. 7. At this time, if the nerves and blood vessel do not exist vertically, a portion between the dermis fat layer 42 and a subcutaneous fat layer 43 of the cut portion is magnified or the inside of the subcutaneous fat layer 43 is magnified, and then, the doctor checks through the endoscope 60 whether or not the nerves and blood vessel exist vertically. If the nerves and blood vessel do not exist vertically, the dermis fat 10 is inserted through the magnified portion.

If the dermis fat 10 is inserted, as shown in FIG. 8, the doctor picks up the skin 40 and the dermis fat 10 from the outside of the penis 20 with tweezers 70 at the same time, and then, fastens the dermis fat 10 around the penis 20 while moving the dermis fat 10.

If the dermis fat 10 is fastened, as shown in FIG. 9, the cut portion is stitched and the surgical operation is finished.

Therefore, by magnifying the penis using the endoscope after removing the pubic hair portion, the penis magnification can be achieved without any injury of the nerves and blood vessel.

Moreover, the penis does not have any seam of wound, and an operation period of time is reduced more than twice compared with conventional operation methods. Harmful side effects due to anesthesia are minimized, and the present invention has no side effects by joining the inserted epidermis fat with the epidermis fat of the penis without any side effects.

As described above, the method for magnifying penis and the method for using endoscope for the same according to the present invention do not show any indication of surgical operation on the penis and have no harmful side effects not by directly applying dermis fat obtained from the patient's hips to the patient's penis but by inserting the magnifying material through the pubic hair portion after cutting the pubic hair portion. Additionally, the present invention can prevent the patient's nerves and blood vessel during the penis magnifying process since the doctor magnifies the penis while checking the condition of the nerves and the blood vessel through the endoscope.

The forgoing embodiments are merely exemplary and are not to be construed as limiting the present invention. The present teachings can be readily applied to other types of apparatuses. The description of the present invention is intended to be illustrative, and not to limit the scope of the claims. Many alternatives, modifications, and variations will be apparent to those skilled in the art.

What is claimed is:

1. A method for magnifying penis comprising the steps of:

removing a patient's pubic hair portion and cutting skin to a dermis fat layer in length of 1–2 cm;

magnifying a portion between epidermis and the dermis fat layer to the penis through the cut portion using a surgical operation tool to secure a space;

inserting an endoscope through the secured space and checking whether or not nerves and blood vessel exist vertically;

inserting a magnifying material through the secured space if the nerves and blood vessel do not exist vertically;

fastening the magnifying material in a proper position while picking up the skin of the penis and magnifying material at the same time if the magnifying material is inserted; and stitching the cut portion when the magnifying material is fastened.

2. The method according to claim 1, wherein the magnifying material is a dermis fat obtained from the patient's hips in a plate shape.

3. The method according to claim 1, in the step of checking whether or not the nerves and blood vessel exist vertically, if the nerves and blood vessel do not exist vertically, further comprising the steps of magnifying a portion between a subcutaneous fat layer of the cut portion and the dermis fat layer or the inside of the subcutaneous fat layer, checking through the endoscope whether or not the nerves and blood vessel exist vertically, and inserting the magnifying material through the magnified portion if the nerves and blood vessel do not exist vertically.

4. A method using an endoscope for magnifying penis, the method comprising the steps of:

magnifying a portion between epidermis and a dermis fat layer after cutting the skin and checking through the endoscope whether or not the nerves and blood vessel exist vertically; and magnifying a portion between a subcutaneous fat layer and the dermis fat layer or the inside of the subcutaneous fat layer, checking through the endoscope whether or not the nerves and blood vessel exist vertically, and inserting the magnifying material if the nerves and blood vessel do not exist vertically.

* * * * *